United States Patent [19]

Secrist, III et al.

[11] Patent Number: 5,008,265

[45] Date of Patent: Apr. 16, 1991

[54] 2-AMINO-7-(ALICYCLOMETHYL)-3H,5H,-PYRROLO[3,2-D]PYRIMIDIN-4-ONES AND PHARMACEUTICAL USES AND COMPOSITIONS CONTAINING THE SAME

[75] Inventors: John A. Secrist, III; John A. Montgomery; Steve E. Ealick, all of Birmingham, Ala.; Mark D. Erion, Livingston; Wayne C. Guida, Fanwood, both of N.J.

[73] Assignee: BioCryst, Inc., Birmingham, Ala.

[21] Appl. No.: 429,099

[22] Filed: Oct. 31, 1989

[51] Int. Cl.$^5$ .................. A61K 31/505; C07D 487/00
[52] U.S. Cl. ..................................... 514/258; 544/280
[58] Field of Search ......................... 544/280; 514/258

[56] References Cited

U.S. PATENT DOCUMENTS 4,921,858  5/1990  Malone et al. ...................... 544/280
4,923,872  5/1990  Kostlan et al. ..................... 544/280

OTHER PUBLICATIONS

Lim et al., J. Org. Chem., vol. 44, No. 22, 979, p. 3826.
Lim et al., Tetrahedron Letters, vol. 21, pp. 1013-1016 (1980).
Lim et al., J. Org. Chem., 48, 780-788 (1983).

*Primary Examiner*—Cecilia Shen
*Attorney, Agent, or Firm*—Wegner, Cantor, Mueller & Player

[57] ABSTRACT

Disclosed is a compound containing a 2-amino-7-(substituted methyl)-3H,5H-pyrrolo[3,2-d]pyrimidin-4-one wherein substituted methyl is —CH$_2$—R wherein R is an optionally substituted alicyclic group, a pharmaceutical composition containing the compound, and a method for the selective suppression of mammalian T-cell function without diminished effect on humoral immunity which involves administering the composition to a mammal.

13 Claims, No Drawings

2-AMINO-7-(ALICYCLOMETHYL)-3H,5H,-PYRROLO[3,2-D]PYRIMIDIN-4-ONES AND PHARMACEUTICAL USES AND COMPOSITIONS CONTAINING THE SAME

The present invention relates to derivatives of 2-amino-3H,5H-pyrrolo[3,2-d]pyrimidin-4-one.

Purine nucleoside phosphorylase (PNP) catalyzes the phosphorolysis of purine nucleosides in a reversible reaction. Individuals who are deficient in PNP exhibit impaired T-cell development, resulting in lowered cell-mediated immunity, but normal B-cell development, resulting in normal humoral immunity. Accordingly, specific inhibitors of PNP that selectively inhibit T-cell development without damaging humoral immunity could be potentially effective against disorders in which activated T-cells are pathogenic.

Accordingly, the present invention is a PNP inhibitor that is a derivative of 2-amino-7-methyl-3H,5H-pyrrolo[3,2-d]pyrimidin-4-one.

In a first aspect of the invention there is provided a compound 2-amino-7-(substituted methyl)-3H,5H-pyrrolo[3,2-d]pyrimidin-4-one (I) wherein substituted methyl is

—CH$_2$—R.

The R group is an optionally substituted alicyclic group. Preferable alicyclic groups include, e.g., single-ring cycloparafins such as cyclopentyl, cyclohexyl, and cycloheptyl, multi-ring cycloparafins such as 1- and 2-adamantyl, 1-norbornanyl, 2-exo-norbornanyl, 2-endo-norbornanyl, 1- and 2-bicyclo[2.2.2]octanyl, 1-, 2-, 3-, 6-, and 8-bicyclo[3.2.1]octanyl, and 1-, 2-, and 3-bicyclo[3.3.1]nonanyl and cycloolefins such as 1- and 2-norbornenyl. Exemples of the preferred compound (I) are 2-amino-7-(2-adamantylmethyl)-3H,5H-pyrrolo[3,2-d]pyrimidin-4-one (IA), 2-amino-7-(1-adamantylmethyl)-3H,5H-pyrrolo[3,2-d]pyrimidin-4-one (IB), 2-amino-7-(cyclopentylmethyl)-3H,5H-pyrrolo[3,2-d]-pyrimidin-4-one (IC), 2-amino-7-(cyclohexylmethyl)-3H,5H-pyrrolo[3,2-d]-pyrimidin-4-one (ID), 2-amino-7-(cycloheptylmethyl)-3H,5H-pyrrolo[3,2-d]pyrimidin-4-one (IE), 2-amino-7-(1-norbornanylmethyl)-3H,5H-pyrrolo[3,2-d]pyrimidin-4-one (IF), 2-amino-7-(2-exo-norbornanylmethyl)-3H,5H-pyrrolo[3,2-d]pyrimidin-4-one (IG), 2-amino-7-(2-endo-norbornanylmethyl)-3H,5H-pyrrolo[3,2-d]pyrimidin-4-one (IH), 2-amino-7-(1-norbornenylmethyl)-3H,5H-pyrrolo[3,2-d]-pyrimidin-4-one (II), 2-amino-7-(2-norbornenylmethyl)-3H,5H-pyrrolo[3,2-d]-pyrimidin-4-one (IJ), 2-amino-7-(1-bicyclo[2.2.2]-octanylmethyl)-3H,5H-pyrrolo[3,2-d]pyrimidin-4-one (IK), 2-amino-7-(1-bicyclo[3.2.1]-octanylmethyl)-3H,5H-pyrrolo[3,2-d]pyrimidin-4-one (IL), and 2-amino-7-(1-bicyclo[3.3.1]nonanylmethyl)-3H,5H-pyrrolo[3,2-d]-pyrimidin-4-one (IM), and 2-amino-7-(1-noradamantyl-methyl)-3H,5H-pyrrolo[3,2-d]-pyrimidin-4-one (IN). In an alternative preferred embodiment the R has one or two substituents selected from the group consisting of halogen, hydroxy, alkoxy, alkyl, or trifluoromethyl. As halogen is preferably mentioned chloro or fluoro. As alkoxy is preferably mentioned lower alkoxy, including methoxy, ethoxy, propoxy and butoxy. As alkyl is preferably mentioned lower alkyl, including methyl, ethyl, propyl and butyl.

In a second aspect of the invention there is provided a method for the selective suppression of mammalian T-cell function without diminished effect on humoral immunity which comprises administering to a mammal the compound (I), whereby said compound inhibits purine nucleoside phosphorylase and thereby T-cell formation.

In a further aspect of the present invention there is provided a pharmaceutical composition for the selective suppression of mammalian T-cell function without diminished effect on humoral immunity which comprises an effective amount of the compound (I) and a pharmaceutically acceptable diluent therefor.

The invention further relates to pharmaceutical compositions suitable for enteral, such as oral or rectal, transdermal and parenteral administration to mammals including man, which are useful to inhibit purine nucleoside phosphorylase activity and for the treatment of disorders responsive thereto, comprising an effective amount of a pharmacologically active compound of the invention, alone or in combination, with one or more pharmaceutically acceptable carriers.

Preferred pharmaceutical compositions are tablets and gelatin capsules comprising the active ingredient together with (a) diluents, e.g., lactose, dextrose, sucrose, mannitol, sorbitol, cellulose and/or glycine; (b) lubricants, e.g., silica, talcum, stearic acid, its magnesium or calcium salt, polyethyleneglycol, or mixtures thereof; for tablets also (c) binders, e.g., magnesium aluminum silicate, starch paste, gelatin, tragacanth, methylcellulose, sodium carboxymethylcellulose, polyvinylpyrrolidone, or mixtures thereof; if desired (d) disintegrants, e.g., starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with a carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

The present invention provides a method of inhibiting purine nucleoside phosphorylase activity in mammals and treating diseases and conditions responsive thereto, e.g., autoimmune disorders, rejection of transplantation or psoriasis, which comprises administering to a mammal in need thereof an effective amount of a compound of the invention or of a pharmaceutical composition comprising a said compound in combination with one or more pharmaceutically acceptable carriers.

A further aspect of the invention relates to a method of inhibiting the phosphorolysis and metabolic breakdown of antiviral or antitumor purine nucleosides in mammals which comprises administering in conjunction therewith to a mammal in need thereof, either separately or in combination therewith, an effective purine nucleoside phosphorylase inhibiting amount of a compound of the invention or of a said compound in combination with one or more pharmaceutically acceptable carriers. More particularly, such relates to a method of inhibiting the phosphorolysis and metabolic breakdown of purine nucleosides known in the art, e.g., of 2'-deoxyguanosine, 2',3'-dideoxyinosine, 2',3'-dideoxyguanosine or 2',3'-dideoxyadenosine.

Furthermore, the invention thus relates to a method of potentiating the antiviral or antitumor effect of 2' or 3'-monodeoxypurine nucleosides or of 2',3'-dideoxypurine nucleosides in mammals which comprises administering in conjunction therewith to a mammal in need thereof, either separately or in combination with a said nucleoside, an effective purine nucleoside phosphorylase inhibiting amount of a compound of the invention preferably in combination with one or more pharmaceutically acceptable carriers. More particularly, such relates to a method of enhancing or potentiating the effect of 2', 3'-dideoxypurine nucleosides known in the art, e.g., of 2', 3'-dideoxyinosine, 2',3'-dideoxyguanosine or 2'-3'-dideoxyadenosine for the treatment of retrovirus infections, e.g., HIV-retrovirus infections (acquired immunodeficiency syndrome, AIDS). 2', 3'-Dideoxypurine nucleosides are known in the art as inhibitors of HIV retrovirus infectivity and to be metabolically degraded by PNP, e.g., as described in *Biochemical Pharmacology* 22, 3797 (1987). Such are administered at a pharmaceutically acceptable dose which is effective in inhibiting HIV-retrovirus infections. Preferably the lowest possible effective dose is used.

The pharmaceutically acceptable effective dosage of active compound of the invention to be administered is dependent on the species of warm-blooded animal (mammal), the body weight, age and individual condition, and on the form of administration.

The pharmaceutical composition may be oral, parenteral, suppository or other form which delivers the compound (I) into the bloodstream of a mammal to be treated. An oral form has from about 1 to about 150 mg of the compound (I) for an adult (50 to 70 kg) which is mixed together with pharmaceutically acceptable diluents such as lactose. In a typical capsule, 25 mg of the compound (I) are mixed together with 192 mg lactose, 80 mg modified starch and 3 mg magnesium stearate. Injectable forms of the compound are also contemplated for administration.

The present invention is also useful with other therapeutic agents. A daily dosage for a human weighing 50 to 70 kg of 1-50 mg/kg inhibits metabolic destruction of certain anticancer agents such as beta-2'-deoxy-6-thioguanosine and antiviral agents such as 2', 3'-dideoxyinosine, an anti-AIDS drug. These types of agents are known to be susceptible to cleavage. Upon cleavage, the agents lose effectiveness. The compounds of the present invention are capable of reducing such cleavage. This protection, therefore, enhances the efficacy of other chemotherapeutic agents.

A preferred method of making the compound (I) of the present invention uses 3-substituted propionitriles as starting materials. Such starting materials can be obtained by a variety of methods that are well documented in the literature. The compound (I) is then prepared from the starting material by an adaptation of the synthetic methodology disclosed in M. I. Lim, R. S. Klein, and J. J. Fox, *J. Org. Chem.*, 44. 3826 (1979); M. I. Lim, R. S. Klein, and J. J. Fox, *Tetrahedron Lett.*, 21, 1013 (1980); M. I. Lim and R. S. Klein, *Tetrahedron Lett.*, 22, 25 (981); M. I. Lim, W. Y. Ren, B. A. Otter, and R. S. Klein, *J. Org. Chem.*, 48, 780 (1983).

In order to more fully describe the present invention the following non-limiting examples are provided. In the examples all parts and percentages are by weight unless indicated otherwise. Proportions of solvent mixtures used as chromatographic eluents are by volume.

EXAMPLE 1

3-(2-Adamantyl)propionitrile is prepared in this example using a modification of the procedure of M. Ohno, et al., *J. Org. Chem.* 53, 1285 (1988). A Solution of 2-bromoadmantane (20 g; 92.96 mmole); Bu$_3$SnH (32.46 g; 111.5 mmole), acrylonitrile (9,86 g; 185.92 mmole), and AIBN (740 mg) in toluene (280 ml) is stirred at reflux temperature for 3 h. The reaction mixture is washed with ammonia water (0.4 M, 500 ml), the organic layer is washed with H$_2$O and dried over MgSO$_4$ and evaporated. The residue is distilled between 110°–118° C. (and about 0.2 mmHg); fractions are combined to give a crude sample of contaminated 3-(2-adamantyl)propionitrile with tin complexes, which is purified on silica gel column with hexanes; followed by hexanes/ethylacetate 97:3 and hexanes/ethylacetate 95:5, yield 9.4 g (53.4%); mp semi-solid.

EXAMPLE 2

3-(2-Adamantyl)propionitrile of Example 1 is further treated in the synthesis of the present invention. Under an atmosphere of dry N$_2$, a mixture of 3-(2-adamantyl)-propionitrile (7.0 g, 36.99 mmole), sodium hydride (1.7 g, 73.95 mmole), and anhydrous tetrahydrofuran (75 ml) is heated at 52° C. in a water bath for 15 min., and a solution of ethyl formate (13.69 g, 184.89 mmole) in THF (100 ml) is added over a period of 45 min. After two hours at 50°-55° C., a second portion of NaH (0.8 g) and HCO$_2$Et (7.5 ml) are added, and the reaction mixture is stirred for about two days. A third portion of HCO$_2$Et (7.5 ml) and NaH (0.8 g) are added and left at room temperature for about 24 hours (unreacted nitrile is inert in the next step and can be recovered at the first purification step). The thick paste is stirred overnight and allowed to cool to room temperature. Volatile matter is evaporated under reduced pressure, and the residual pale yellow crust is dissolved in the minimum volume of cold water (appr. 150 ml) at 0° C. The solution is adjusted to pH 6.0 by addition of 6 N HCl and extracted with CHCl$_3$ (3×100 ml). The extract is washed with H$_2$O, dried over Na$_2$SO$_4$, and evaporated in vacuo to a thick amber oil. This crude product is used in the next reaction without further purification.

EXAMPLE 3

Glycine methyl ester hydrochloride (6.96 g, 55.46 mmole) and anhydrous sodium acetate (4.55 g, 55.46 mmole) are added to a solution of the crude formyl compound (8.0 g) in MeOH/H$_2$O (4:1, 500 ml). After 24 hours, the MeOH is evaporated in vacuo, and the mixture of water and oil is extracted with CHCl$_3$. The CHCl$_3$ layer is dried (Na$_2$SO$_4$) and evaporated to give an amber oil which is applied to a silica gel column. Elution with CHCl$_3$ gave two major bands: (1) 3-(2-adamantyl)-propionitrile (used as starting material in the previous step), and (2) the desired enamine; yield 6 g.

EXAMPLE 4

Under a nitrogen atmosphere, ethyl chloroformate (2.82 g, 26.0 mmole) is added dropwise to a solution of the enamine of Example 3 (5.0 g, 17.34 mmole) and 1,5-diazabicyclo-[4.3.0]non-5-ene ("DBN," 6.46 g, 52.0 mmole) in dry $CH_2Cl_2$ (50 ml) with external cooling in an ice bath. After stirring at 0° C. for one hour, the solution is allowed to a stand at room temperature overnight. After checking progress by TLC, additional $ClCO_2Et$ (1.81 ml) and DBN (3.23 g) are added to complete the conversion, and the solution is allowed to stand for 24 hours. Volatile matter is evaporated in vacuo, the viscous residue purified on a short silica gel column (whose main purpose is to remove the less-mobile DBN) to give an N-blocked pyrrole, which is used for the next step without further purification.

EXAMPLE 5

To a solution of the crude N-blocked pyrrole of Example 4 (6.0 g, 16.59 mmole) in MeOH (100 ml) is added solid $Na_2CO_3$ (4.39 g, 41.49 mmole), and the reaction mixture is stirred at room temperature for 48 hr with separation of the resultant deblocked pyrrole. The mixture is evaporated to dryness, and the residue is triturated thoroughly with $H_2O$ (50 ml) to dissolve inorganics and extracted with $CHCl_3$ (3×100 ml). The extract is dried ($Na_2SO_4$) and evaporated to give a viscous gum, which crystallized by triturating with ether; yield 4 g; m.p. 162°-163° C.

EXAMPLE 6

Benzoyl isothiocyanate (1.22 g, 7.47 mmole) is added dropwise to a solution of the unblocked pyrrole of Example 5 (1.91 g, 6.62 mmole) in dry $CH_2Cl_2$ (50 ml). After 1 h at room temperature, solution is evaporated, and the gummy residue is dissolved in $Et_2O$ (100 ml) with almost immediate separation of the crystalline solid. The $Et_2O$ filtrate is heated to boiling and diluted with an equal volume of warm cyclohexane. On cooling slowly the solution gives additional thioureido product; yiled 2.81 g (95%); m.p 193°-194° C.

EXAMPLE 7

Methyl iodide (2.46 g, 17.39 mmole) is added to a solution of the thioureido product of Example 6 (2.7 g, 5.98 mmole) and DBN (0.82 g, 6.57 mmole) in dry $CH_2Cl_2$ (50 ml) at 0° C. The solution is stirred at 0° C. for 15 min., at ambient temperature for 1 h, and then evaporated in vacuo to give a crude sample of the methythio intermediate compound; yield 2.78 g (crude).

EXAMPLE 8

A solution of the methylthio compound of Example 7 (2.78 g, 5.18 mmole) in 150 ml of MeOH that has been saturated with $NH_3$ at 0° C. is heated at 90°-95° C. for 24 hours in a glass-lined stainless steel bomb. The contents of the chilled bomb are evaporated in vacuo to give a mixture of the compound (IA), benzamide and a by-product that is a 2-methylthio derivative, as opposed to the 2-amino compound (IA). The mixture is stirred vigorously for several minutes with appr. 75 ml of $Et_2O$, and the insoluble white solid is filtered off and washed with $Et_2O$. The filtrate contained most of the benzamide and 2-methylthio components. A solution of the $Et_2O$-insoluble solid (1.38 g) in MeOH is evaporated with appr. 25 g of silica gel. The powdered residue is layered evenly onto the top of a silica gel column, which is then eluted with $CHCl_3$/MeOH/HOAc (95:5:1) to give the 2-methylthio by-product and the desired 2-amino product (IA). (IA) is recrystallized by extraction into boiling isopropyl acetate in a Soxhlet apparatus. The white crystals are collected in three crops and dried in vacuo over $P_2O_5$ at 110° C. for 7 h; yield 51.6%; mp>350° C. dec.; anal. calcd. for $C_{17}H_{22}N_4O \cdot 0.21 MeOH \cdot 0.22 H_2O$: C, 66.88; H, 7.59; N, 18.12. Found: C, 66.86; H, 7.59; N, 18.12.

EXAMPLE 9

The compound of Example 8 is tested for enzyme inhibition activity. A purine nucleoside phosphorylase (PNP) enzyme assay is performed in which the PNP activity ($IC_{50}$) for the compound is found, which is determined radiochemically by measuring the formation of [$^{14}C$]-hypoxanthine from [$^{14}C$]-inosine (see *Biomedicine*, 33, 39 (1980)) using calf spleen as the enzyme source. At 1 mM phosphate the $IC_{50}$ is 0.090 μM, and at 50 mM phosphate the $IC_{50}$ is 2.5 μM.

EXAMPLES 10-14

The following compounds of the present invention are prepared that are 2-amino-7-(substituted methyl)-3H,5H-pyrrolo[3,2-d]-pyrimidin-4-ones wherein substituted methyl is —$CH_2$—R in which the R group is a 2-adamantyl group as follows:

Example 10 R=2-(1-methyl)-adamantyl
Example 11 R=2-(1-chloro)-adamantyl
Example 12 R=2-(1-trifluoromethyl)-adamantyl
Example 13 R=2-(1-methoxy)-adamantyl
Example 14 R=2-(1-fluoro)-adamantyl The compounds are prepared following the procedures set forth in Examples 2-8 using the appropriate 3-(2-adamantyl)-propionitriles as starting materials.

EXAMPLES 15-20

The following compounds of the present invention are prepared that are 2-amino-7-(substituted methyl)-3H,5H-pyrrolo[3,2-d]-pyrimidin-4-ones wherein substituted methyl is —$CH_2$—R in which the R group is a 1-adamantyl group as follows:

Example 15 R=1-(2-methyl)-adamantyl
Example 16 R=1-(2-chloro)-adamantyl
Example 17 R=1-(2-trifluoromethyl)-adamantyl
Example 18 R=1-(2-methoxy)-adamantyl
Example 19 R=1-(2-fluoro)-adamantyl
Example 20 R=1-adamantyl The compounds are prepared following the procedures set forth in Examples 2-8 using the appropriate 3-(1-adamantyl)-propionitriles as starting materials.

EXAMPLE 21

A pharmaceutical composition for intraperitoneal injection is prepared for testing the compound (IA). An intraperitoneal injection solution containing the compound (IA) is dissolved in an aqueous carrier that contains ten percent DMSO.

EXAMPLE 22

The compound (IA) is intraperitoneally injected into Lewis Rats via the test composition of Example 21 to provide 30 mg of the compound (IA), with an injection given twice per day. Controls are used, which receive only the vehicle. At specific times after administration, the animals are sacrificed and plasma samples are prepared. The plasma is extracted with cold 0.5 N HClO₄ and neutralized with solid NH₄HCO₃. After removal of perchlorate salts, the extract is subjected to HPLC on a reversed phase column (Spherisorb ODSI). A significant increase in plasma inosine is observed in the plasma taken from animals receiving the compound (IA).

EXAMPLES 23-33

Compounds prepared as in Examples 10-20 are each made into a pharmaceutical formulation in accordance with the preparation of Example 21 and the resultant injectable solutions are tested in accordance with the procedure of Example 22. A significant increase in plasma inosine is observed in the plasma taken from animals receiving the compounds of the present invention.

EXAMPLE 34

3-Cyclopentylpropionitrile is prepared in this example. 3-Cyclopentylpropionyl chloride (57.7 g, 0.36 mole) is added dropwise to a large excess of concentrated ammonium hydroxide (400 ml) cooled in an ice/salt bath. The heavy suspension of white solid is stirred overnight, collected by filtration, washed with cold water, and recrystallized from about 2 liters of boiling water. The lustrous white plates of the amide are dried in vacuo over $P_2O_5$; yield 31.6 g (62.3%); mp 122° C.

With protection from atmospheric moisture, a solution of the amide (23.5 g, 0.166 mole) in POCl₃ (150 ml) is heated at 120° C. for 1 h. The oil bath is cooled to about 70° C., and excess POCl₃ is distilled off under vacuum, and the cooled residue is poured onto ice (about 300 g). The mixture is neutralized by cautious addition of solid Na₂CO₃ and extracted with several portions of Et₂O. The dried (Na₂SO₄) extract is evaporated to give a clear, pale yellow oil which is distilled in vacuo to give the desired nitrile; yield, 16.86 g (82%) bp 88.0°-88.5° C./8.7 mm). MS (EI): m/z 122 (M-H)⁺; IR (cap. film), 2245 cm⁻¹(CN); ¹H NMR, δ 1.67 (q, 2, —CH₂CH₂CN), 2.36 (t, 2, —CH₂CN), complex multiplets centered about 1.11, 1.63, 1.86 (cyclopentyl protons).

EXAMPLE 35

3-Cyclopentylpropionitrile of the previous example is further treated in the synthesis of the present invention. Under an atmosphere of dry N₂, a mixture of 3-cyclopentylpropionitrile (14.8 g, 0.12 mole), sodium hydride (5.8, 0.24 mole), and anhydrous tetrahydrofuran (300 ml) is heated at 52° C. in a water bath for 15 min., and a solution of ethyl formate (13.3 g, 0.18 mole) in THF (100 ml) is added over a period of 45 min. After two hours at 50°-55° C., a second portion of NaH (1.9 g) and HCO₂Et (5.0 ml) are added, followed in 30 min. by a third portion of HCO₂Et (unreacted nitrile is inert in the next step and can be recovered at the first purification step). The thick paste is stirred overnight and allowed to cool to room temperature. Volatile matter is evaporated under reduced pressure, and the residual pale yellow crust is dissolved in the minimum volume of cold water (about 150 ml) at 0° C. The solution is adjusted to pH 6.0 by addition of 6 N HCl and extracted with CHCl₃ (3×100 ml). The extract is washed with H₂O, dried over Na₂SO₄, and evaporated in vacuo to a thick amber oil. This crude product (15.6 g) is used in the next reaction without further purification.

EXAMPLE 36

Glycine methyl ester hydrochloride (19.31 g, 0.154 mole) and anhydrous sodium acetate (12.61 g, 0.154 mole) are added to a solution of the crude formyl compound of the previous example (15.6 g) in MeOH/H₂O (4:1, 500 ml). After 24 hours, the MeOH is evaporated in vacuo, and the mixture of water and oil is extracted with CHCl₃. The CHCl₃ layer is dried (Na₂SO₄) and evaporated to give an amber oil which is applied to a silica gel column. Elution with CHCl₃ gave two major bands: (1) 3-cyclopentylpropionitrile (8.22 g, 66.7 mmole or 55.6% of the nitrile used as starting material in the previous step), and (2) the desired enamine (3.45 g; 29.1% based on theoretical yield corrected for amount of nitrile present in starting material; MS (FAB): 223 (M+H)⁺).

EXAMPLE 37

Under a nitrogen atmosphere, ethyl chloroformate (2.53 g, 23.3 mmole) is added dropwise to a solution of the enamine of the previous example (3.45 g, 15.5 mmole) and DBN (5.78 g, 46.6 mmole) in dry CH₂Cl₂ (50 ml) with external cooling in an ice bath. After stirring at 0° C. for one hour, the solution is allowed to a stand at room temperature overnight. After checking progress by TLC, additional ClCO₂Et (0.5 ml) and DBN (3.0 ml) are added to complete the conversion, and the solution is allowed to stand for 24 hours. Volatile matter is evaporated in vacuo, the viscous residue purified on a short silica gel column (whose main purpose is to remove the less-mobile DBN) to give an N-blocked pyrrole (4.50 g; 98%), which is used for the next step without further purification.

EXAMPLE 38

To a solution of the N-blocked pyrrole of the previous example (4.50 g, 15.3 mmole) in MeOH (100 ml) is added solid Na₂CO₃ (1.62 g, 15.3 mmole), and the reaction mixture is stirred at room temperature for 48 hr with separation of the resultant deblocked pyrrole. The mixture is evaporated to dryness, and the residue is triturated thoroughly with H₂O (50 ml) to dissolve the inorganics and extracted with CHCl₃ (3×100 ml). The extract is dried (Na₂SO₄) and evaporated to give a viscous gum that crystallized upon drying in vacuo; yield 2.97 g (87.4%) of material suitable for use as an intermediate without further purification. More extensive purification can, however, be effected by using either column chromatography employing silica gel/CHCl₃ or recrystalization from toluene/cyclohexane (1:3).

EXAMPLE 39

Benzoyl isothiocyanate (2.62 g, 16.03 mmole) is added dropwise to a solution of the unblocked pyrrole of Example 38 (2.97 g, 13.36 mmole) in dry CH₂Cl₂ (100 ml). After 1 h at room temperature, solution is evaporated, and the gummy residue is dissolved in Et₂O (100 ml) with almost immediate separation of crystalline solid; yield 1.75 g. The Et₂O filtrate is heated to boiling and diluted with an equal volume of warm cyclohexane. On cooling slowly the solution gave an additional 1.58 g of thioureido product; total yield 3.33 g (64.6%). A small amount of the thioureido product is recrystallized from warm Et₂O/cyclohexane (15 ml each); mp 123°-125° C. MS (FAB): 386 (M+H)⁺. Anal. Calcd, for $C_{20}H_{23}N_3O_3S \cdot 0.45C_6H_{12}$: C, 64.40; H, 6.76; N, 9.93. Found: C, 64.51; H, 7.10; N, 9.93.

EXAMPLE 40

Methyl iodide (2.60 g, 18.32 mmole) is added to a solution of the thioureido product of Example 39 (3.21 g, 8.33 mmole) and DBN (1.24 g, 9.99 mmole) in dry $CH_2Cl_2$ (80 ml) at 0° C. The solution is stirred at 0° C. for 15 min., at ambient temperature for 1 h, and then evaporated in vacuo. A solution of the residue in $CHCl_3$ is chromatographed on a silica gel column with $CHCl_3$ as eluent to give homogeneous fractions of the methylthio intermediate compound; yield, 2.46 g (74%).

EXAMPLE 41

A solution of the methylthio compound of Example 40 (2.07 g, 5.18 mmole) in 150 ml of MeOH that has been saturated with $NH_3$ at 0° C. is heated at 90°–95° C. for 24 hours in a glass-lined stainless steel bomb. The contents of the chilled bomb are evaporated in vacuo to give a mixture of the compound (IC), benzamide and a by-product that is a 2-methylthio derivative, as opposed to the 2-amino compound (IC). The mixture is stirred vigorously for several minutes with appr. 75 ml of $Et_2O$, and the insoluble white solid is filtered off and washed with $Et_2O$. The filtrate contained most of the benzamide and 2-methylthio components. A solution of the $Et_2O$-insoluble solid (1.13 g) in MeOH is evaporated with appr. 10 g of silica gel. The powdered residue is layered evenly onto the top of a silica gel column, which is then eluted with $CHCl_3$/MeOH/HOAc (95:5:1) to give the 2-methylthio by-product (252 mg; MS (FAB): 264 $(M+H)^+$) and the desired 2-amino product (IC) (679 mg, 56.4%). (IC) is recrystallized by extraction into boiling isopropyl acetate in a Soxhlet apparatus. The white crystals are collected in three crops and dried in vacuo over $P_2O_5$ at 110° C. for 7 h; yield 540 mg (44.9%); mp 324°–326° C. dec.; MS (FAB): 233 $(M+H)^+$; anal. calcd. for $C_{12}H_{16}N_4O$: C, 62.05; H, 6.94; N, 24.12. Found: C, 62.04; H, 7.11; N, 24.48.

EXAMPLE 42

The compound of Example 41 is tested for enzyme-inhibition activity in accordance with the procedure of Example 9. At 1 mM phosphate the $IC_{50}$ is 0.029 $\mu M$, and at 50 mM phosphate the $IC_{50}$ is 1.8 $\mu M$.

EXAMPLES 43–46

The following compounds of the present invention are prepared that are 2-amino-7-(substituted methyl)-3H,5H-pyrrolo[3,2-d]-pyrimidin-4-ones wherein substituted methyl is —$CH_2$—R in which the R group is as follows:
Example 43 R=3-methylcyclopentyl
Example 44 R=2-chlorocyclopentyl
Example 45 R=3-triflouromethylcyclopentyl
Example 46 R=3-methoxycyclopentyl The compounds are prepared following the procedures set forth in Examples 34–41 using the appropriate 3-(substituted cyclopentyl)-propionitriles as starting materials.

EXAMPLE 47

A pharmaceutical composition for intraperitoneal injection is prepared for testing the compound (IC). An intraperitoneal injection solution is prepared containing the compound (IC) is dissolved in an aqueous carrier that contains ten percent DMSO.

EXAMPLE 48

Using the procedure of Example 16, the compound (IC) is intraperitoneally injected into Lewis Rats via the test composition of Example 47 and the results compared with controls. A significant increase in plasma inosine is observed in the plasma taken from animals receiving the compound (IC).

EXAMPLE 49

3-Cyclohexylpropionitrile is prepared in this example. A solution of cyclohexanepropionic acid (50 g; 0.32 mole) and thionyl chloride (152 g; 1.28 mole) in 100 ml benzene is allowed to stand overnight and is then evaporated to an oily residue. The residue is added in portions to 28% aqueous ammonia (270 ml) at 25° C. and the mixture stirred for about two hours. The resulting product is collected by filtration, washed with cold water, and recrystallized from about 2 liters of boiling water. The lustrous white plates of the amide are dried in vacuo over $P_2O_5$; yield 45.5 g.

With protection from atmospheric moisture, a solution of the amide (45.5 g, 0.293 mole) in $SOCl_2$ (200.3 g; 1.68 mole) refluxed for about six hours. The oil bath is cooled to about 70° C., and excess $SOCl_2$ is distilled off under vacuum, and the cooled residue is poured onto ice (about 300 g). The mixture is neutralized by cautious addition of solid $Na_2CO_3$ and extracted with several portions of $Et_2O$. The dried ($Na_2SO_4$) extract is evaporated to give a clear, pale yellow oil which is distilled in vacuo to give the desired nitrile; yield 42.0 g.

EXAMPLE 50

3-Cyclohexylpropionitrile of Example 49 is further treated in the synthesis of the present invention. Under an atmosphere of dry $N_2$, a mixture of 3-cyclohexylpropionitrile (22.3 g, 0.16 mole), sodium hydride (5.38, 0.224 mole), and anhydrous tetrahydrofuran (120 ml) is heated at 52° C. in a water bath for 15 min., and a solution of ethyl formate (55.4 g, 0.75 mole) in THF (50 ml) is added over a period of 45 min. After two hours at 50°–55° C., a second portion of NaH (2.0 g) and $HCO_2Et$ (5.0 ml) are added (unreacted nitrile is inert in the next step and ca be recovered at the first purification step), and the reaction mixture is stirred for about three days at 55° C. and then allowed to cool to room temperature. Volatile matter is evaporated under reduced pressure, and the residual pale yellow crust is dissolved in the minimum volume of cold water (about 75 ml) at 0° C. The solution is adjusted to pH 6.0 by addition of 6 N HCl and extracted with $CHCl_3$ (3 × 100 ml). The extract is washed with $H_2O$, dried over $Na_2SO_4$, and evaporated in vacuo to a thick amber oil. This crude product is used in the next reaction without further purification.

EXAMPLE 51

Glycine methyl ester hydrochloride (30.60 g, 0.24 mole) and anhydrous sodium acetate (19.99 g, 0.24 mole) are added to a solution of the crude formyl compound of the previous example (25.22 g) in MeOH/$H_2O$ (4:1, 500 ml). After 24 hours, the MeOH is evaporated in vacuo, and the mixture of water and oil is extracted with $CHCl_3$. The $CHCl_3$ layer is dried ($Na_2SO_4$) and evaporated to give an amber oil which is applied to a silica gel column. Elution with $CHCl_3$ gave two major bands: (1) 3-cyclohexylpropionitrile (used as starting material in the previous step), and (2) the desired enamine; yield 16 g.

EXAMPLE 52

Under a nitrogen atmosphere, ethyl chloroformate (1.38 g, 12.7 mmole) is added dropwise to a solution of the enamine of Example 51 (2.0 g, 8.46 mmole) and DBN (2.1 g, 16.9 mmole) in dry $CH_2Cl_2$ (50 ml) with external cooling in an ice bath. After stirring at 0° C. for one hour, the solution is allowed to a stand at room temperature overnight. After checking progress by TLC, additional $ClCO_2Et$ (0.5 ml) and DBN (1.5 ml) are added to complete the conversion, and the solution is allowed to stand for 24 hours. Volatile matter is evaporated in vacuo, the viscous residue purified on a short silica gel column (whose main purpose is to remove the less-mobile DBN) to give an N-blocked pyrrole, which is used for the next step without further purification.

EXAMPLE 53

To a solution of the N-blocked pyrrole of Example 52 (2.6 g, 8.43 mmole) in MeOH (100 ml) is added solid $Na_2CO_3$ (2.23 g, 21.07 mmole), and the reaction mixture is stirred at room temperature for 48 hr with separation of the resultant deblocked pyrrole. The mixture is evaporated to dryness, and the residue is triturated thoroughly with $H_2O$ (50 ml) to dissolve inorganics and extracted with $CHCl_3$ (3×100 ml). The extract is dried ($Na_2SO_4$) and evaporated to give a viscous gum, which is purified on a silica gel column using $CHCl_3$ as the eluent; yield 1.67 g (84%); m.p. 73°–74° C.

EXAMPLE 54

Benzoyl isothiocyanate (0.74 g, 4.02 mmole) is added dropwise to a solution of the unblocked pyrrole of Example 53 (0.95 g) in dry $CH_2Cl_2$ (20 ml). After one hour at room temperature, the solution is evaporated, and the gummy residue is dissolved in $Et_2O$ (100 ml) with almost immediate separation of crystalline solid. The $Et_2O$ filtrate is heated to boiling and diluted with an equal volume of warm cyclohexane. On cooling slowly the solution gives additional thioureido product; total yield 1.41 g (88%); m.p. 156°–157° C.

EXAMPLE 55

Methyl iodide (1.1 g, 7.6 mmole) is added to a solution of the thioureido product of Example 54 (0.96 g, 2.61 mmole) and 1,5-diazabicyclo[4.3.0]non-5-ene (0.38 g, 3.0 mmole) in dry $CH_2Cl_2$ (20 ml) at 0° C. The solution is stirred at 0° C. for 15 min., at ambient temperature for 1 h, and then evaporated in vacuo. A solution of the residue in $CHCl_3$ is chromatographed on a silica gel column with $CHCl_3$ as eluent to give homogeneous fractions of the methylthio intermediate compound; yield 0.92 g.

EXAMPLE 56

A solution of the methylthio compound of Example 55 (0.8 g, 1 93 mmole) in 50 ml of MeOH that has been saturated with $NH_3$ at 0° C. is heated at 90°–95° C. for 24 hours in a glass-lined stainless steel bomb. The contents of the chilled bomb are evaporated in vacuo to give a mixture of the compound (ID), benzamide and a by-product that is a 2-methylthio derivative, as opposed to the 2-amino compound (ID). The mixture is stirred vigorously for several minutes with appr. 75 ml of $Et_2O$, and the insoluble white solid is filtered off and washed with $Et_2O$. The filtrate contained most of the benzamide and 2-methylthio components. A solution of the $Et_2O$-insoluble solid (0.390 g) in MeOH is evaporated with appr. 10 g of silica gel. The powdered residue is layered evenly onto the top of a silica gel column, which is then eluted with $CHCl_3/MeOH/HOAc$ (95:5:1) to give the 2-methylthio by-product and the desired 2-amino product (ID). (ID) is recrystallized by extraction into boiling isopropyl acetate in a Soxhlet apparatus. The white crystals are collected in three crops and dried in vacuo over $P_2O_5$ at 110° C. for 7 h; yield 49%, mp>300° C.; anal. calcd. for $C_{13}H_{18}N_4O$: C, 63.39, H, 7.36; N, 22.74. Found: C, 63.50; H, 7.74; N, 22.67.

EXAMPLE 57

The compound of Example 56 is tested for enzyme inhibition activity as in Example 9. At 1 mM phosphate the $IC_{50}$ is 0.037 μM, and at 50 mM phosphate the $IC_{50}$ is 2.2 μM.

EXAMPLE 58

The compound of Example 56 is tested to determine its effectiveness in potentiation of the toxicity of 2'-deoxyguanosine (d-Guo) (see D. A. Schewach et al., Cancer Res., 46, 519 (1986), and J. C. Sircar et al., Agents and Actions, 21, 253 (1987)). CCRF-CEM cells are grown in RPMI-1640 medium. To a suspension cultures of these cells, d-Guo at a fixed concentration (5.62 μM) and the compound at varied concentrations are added and the number of cells are determined in a Coulter counter 24, 48, and 72 hours thereafter. From these data, the $IC_{50}$ is calculated to be 2.0 μM as the concentration of the compound required to reduce the increase in cell number between 0 and 72 hours to 50% of that of control cultures.

EXAMPLE 59

The compound 2-amino-7-(3-methylcyclohexylmethyl)-3H,5H-pyrrolo[3,2-d]pyrimidin-4-one is prepared. First, using the procedures set forth in Examples 50–56 above, but with 3-(3-methylbenzyl)-propionitrile as the starting material, the aryl derivative 2-amino-7-(3-methylbenzyl)-3H,5H-pyrrolo[3,2-d]-pyrimidin-4-one is made. A solution of the aryl derivative (0.2 g, 0.78 mmole) in trifluoroacetic acid (TFA) (20 ml) is hydrogenated with $PtO_2$ at 60 lb/in² for 24 h. Catalyst is filtered off through a Celite bed, and the filtrate is evaporated. The residue is triturated with methanol and left in the refrigerator overnight. The resulting crystallized trifluoroacetate salt precipitates from the solution and is collected by filtration. The TFA salt is suspended in 8 ml of $H_2O$, adjusted to pH8 by conc. $NH_4OH$ and sonicated. The pure product is collected, washed with $H_2O$ and dried: yield 165 mg (81%); mp 282° C. Anal: Calcd. for $C_{14}H_{20}N_4O$: C, 64.60; H, 7.74; N, 21.52. Found: C, 64.24; H, 7.96; N, 21.51%.

EXAMPLE 60

The procedure described in Example 59 is repeated to prepare 2-amino-7-(3-trifluoromethylcyclohexylmethyl)-3H,5H-pyrrolo[3,2-d]pyrimidin-4-one using 3-(3-trifluoromethylbenzyl)propionitrile as the starting compound: yield 69%; mp 165° C. Anal. calcd. for $C_{14}H_{17}N_4OF_3\cdot 0.6H_2O$: C, 51.72; H, 5.64; N, 17.23. Found: C, 51.82; H, 5.71; N, 16.81%.

EXAMPLE 61

The compound prepared in Example 59 is tested for enzyme-inhibition activity as in Example 9. At 1 mM phosphate the $IC_{50}$ is 0.025 μM, and at 50 mM phosphate the $IC_{50}$ is 0.0.820 μM.

EXAMPLE 62

The compound prepared in Example 60 is tested for enzyme-inhibition activity as in Example 9. At 1 mM phosphate the $IC_{50}$ is 0.020 μM, and at 50 mM phosphate the $IC_{50}$ is 0.740 μM.

EXAMPLE 63

3-Cycloheptylpropionitrile is prepared in this example according to the procedure of Example 1 using a solution of 2-bromocycloheptane (25.57 g; 144.38 mmole); $Bu_3SnH$ (50.42 g; 173.26 mmole), acrylonitrile (15.32 g; 288.77 mmole), and AIBN (1.13 g) in toluene (300 ml). Yield is 16 g; mp oil.

EXAMPLE 64

3-Cycloheptylpropionitrile of Example 63 is further treated in the synthesis of the present invention. Under an atmosphere of dry $N_2$, a mixture of 3-cycloheptylpropionitrile (8.5 g, 56.19 mmole), sodium hydride (2.6 g, 112.39 mmole), and anhydrous tetrahydrofuran (100 ml) is heated at 52° C. in a water bath for 15 min., and a solution of ethyl formate (20.81 g, 280.99 mmole) in THF (100 ml) is added over a period of 45 min. After two hours at 50°-55° C., a second portion of NaH (1.35 g) and $HCO_2Et$ (10.4 g) are added, followed in 30 min. by a third portion of $HCO_2Et$ (unreacted nitrile is inert in the next step and can be recovered at the first purification step). The thick paste is stirred overnight and allowed to cool to room temperature. Volatile matter is evaporated under reduced pressure, and the residual pale yellow crust is dissolved in the minimum volume of cold water (about 150 ml) at 0° C. The solution is adjusted to pH 6.0 by addition of 6 N HCl and extracted with $CHCl_3$ (3×100 ml). The extract is washed with $H_2O$, dried over $Na_2SO_4$, and evaporated in vacuo to a thick amber oil. This crude product is used in the next reaction without further purification.

EXAMPLE 65

Glycine methyl ester hydrochloride (9.35 g, 74.47 mmole) and anhydrous sodium acetate (6.10 g, 74.47 mmole) are added to a solution of the crude formyl compound of Example 64 (8.9 g; 49.65 mmole) in $MeOH/H_2O$ (4:1, 250 ml). After 24 hours, the MeOH is evaporated in vacuo, and the mixture of water and oil is extracted with $CHCl_3$. The $CHCl_3$ layer is dried ($Na_2SO_4$) and evaporated to give an amber oil which is applied to a silica gel column. Elution with $CHCl_3$ gave two major bands: (1) 3-cycloheptylpropionitrile (used as starting material in the previous step), and (2) the desired enamine, which is recrystallized from a $CHCl_3/Et_2O$ mixture; yield 6.18 g; m.p. 57°-58° C.

EXAMPLE 66

Under a nitrogen atmosphere, ethyl chloroformate (4.01 g, 37.03 mmole) is added dropwise to a solution of the enamine of Example 65 (6.18 g, 24.69 mmole) and DBN (9.19 g, 74.04 mmole) in dry $CH_2Cl_2$ (100 ml) with external cooling in an ice bath. After stirring at 0° C. for one hour, the solution is allowed to a stand at room temperature overnight. After checking progress by TLC, additional $ClCO_2Et$ (0.5 ml) and DBN (3.0 ml) are added to complete the conversion, and the solution is allowed to stand for 24 hours. Volatile matter is evaporated in vacuo, the viscous residue purified on a short silica gel column (whose main purpose is to remove the less-mobile DBN) to give an N-blocked pyrrole, which is used for the next step without further purification.

EXAMPLE 67

To a solution of the N-blocked pyrrole of Example 66 (7.8 g, 24.19 mmole) in MeOH (100 ml) is added solid $Na_2CO_3$ (6.41 g, 60.48 mmole), and the reaction mixture is stirred at room temperature for 48 hr with separation of the resultant deblocked pyrrole. The mixture is evaporated to dryness, and the residue is triturated thoroughly with $H_2O$ (50 ml) to dissolve inorganics and extracted with $CHCl_3$ (3×100 ml). The extract is dried ($Na_2SO_4$) and evaporated to give a viscous gum, which was purified by column chromatography employing silica gel/$CHCl_3$; yield 4 g; m.p. 88°-89° C.

EXAMPLE 68

Benzoyl isothiocyanate (1.5 g, 8.96 mmole) is added dropwise to a solution of the unblocked pyrrole of Example 67 (1.99 g, 7.95 mmole) in dry $CH_2Cl_2$ (50 ml). After 1 h at room temperature, solution is evaporated, and the gummy residue is dissolved in $Et_2O$ (100 ml) with almost immediate separation of the crystalline solid. The $Et_2O$ filtrate is heated to boiling and diluted with an equal volume of warm cyclohexane. On cooling slowly the solution gives additional thioureido product; yield 2.89 g (88%); m.p. 158°-159° C.

EXAMPLE 69

Methyl iodide (1.7 g, 11.96 mmole) is added to a solution of the thioureido product of Example 68 (1.7 g, 4.1 mmole) and DBN (0.56 g, 4.52 mmole) in dry $CH_2Cl_2$ (80 ml) at 0° C. The solution is stirred at 0° C. for 15 min., at ambient temperature for 1 h, and then evaporated in vacuo. A solution of the residue in $CHCl_3$ is chromatographed on a silica gel column with $CHCl_3$ as eluent to give homogeneous fractions of the methylthio intermediate compound.

EXAMPLE 70

A solution of the methylthio compound of Example 69 (1.72 g, 4.02 mmole) in 50 ml of MeOH that has been saturated with $NH_3$ at 0° C. is heated at 90°-95 ° C. for 24 hours in a glass-lined stainless steel bomb. The contents of the chilled bomb are evaporated in vacuo to give a mixture of the compound (IE), benzamide and a by-product that is a 2-methylthio derivative, as opposed to the 2-amino compound (IE). The mixture is stirred vigorously for several minutes with appr. 75 ml of $Et_2O$, and the insoluble white solid is filtered off and washed with $Et_2O$. The filtrate contained most of the benzamide and 2-methylthio components. A solution of the $Et_2O$-insoluble solid (0.850 g) in MeOH is evaporated with appr. 10 g of silica gel. The powdered residue is layered evenly onto the top of a silica gel column, which is then eluted with $CHCl_3/MeOH/HOAc$ (95:5:1) to give the 2-methylthio by-product and the desired 2-amino product (IE). (IE) is recrystallized by extraction into boiling isopropyl acetate in a Soxhlet apparatus. The white crystals are collected in three crops and dried in vacuo over $P_2O_5$ at 110° C. for 7 h; yield 54%, mp>300° C. dec.; anal. calcd. for $C_{14}H_{20}N_4O$: C, 64.60; H, 7.74; N, 21.52. Found: C, 64.78; H, 8.01; N, 21.61.

EXAMPLE 71

The compound of Example 70 is tested for enzyme inhibition activity as in Example 9. At 1 mM phosphate the $IC_{50}$ is 0.030 μM, and at 50 mM phosphate the $IC_{50}$ is 0.840 μM.

EXAMPLE 72

Using the procedure of Example 1, 3-(1-norbornanyl)propionitrile is made from 1-bromonorbornane, and 3-(2-norbornanyl)-propionitrile (mixture of 2-exo and 2-endo) is made from 2-bromonorbornane. Following Examples 2-8, the propionitriles are converted to the compounds (IF), I(G), and (IH).

EXAMPLE 73

Using the procedure of Example 1, 3-(1-bicyclo[3.2.1]octanyl)-propionitrile, 3-(2-bicyclo-[3.2.1]octanyl)-propionitrile, 3-(3-bicyclo-[3.2.1]octanyl)-propionitrile, and 3-(8-bicyclo-[3.2.1]octanyl)-propionitrile are made respectively from 1-bromo-bicyclo[3.2.1]octane, 2-bromo-bicyclo[3.2.1]octane, 3-bromo-bicyclo[3.2.1]octane, and 8-bromo-bicyclo[3.2.1]octane. Following Examples 2-8, the propionitriles are converted to the compound (IL) and the related 2-bicyclo[3.2.1]octanyl, 3-bicyclo[3.2.1]octanyl, and 8-bicyclo[3.2.1]octanyl derivatives.

EXAMPLE 74

Using a modification of the procedure disclosed in D. Farcasiu, *Synthesis,* 615 (1972), 6-bicyclo[3.2.1]octanecarboxaldehyde is prepared by reacting bicyclo[3.2.1]octan-6-one with trimethylsulfoxonium iodide, giving an intermediate epoxide, which is then converted to the aldehyde by treatment with boron trifluoride etherate. Following the procedure of Netherlands Pat. 6,610,204, the aldehyde is condnesed with cyanoacetic acid by refluxing in a pyridene/toluene solution with a catalytic quantity of ammonium acetate for 48-72 hours to give the corresponding acrylonitrile. The actrylonitrile is then hydrogenated using a palladium-on-carbon catalyst in methanol as taught in Profitt, et al, *J. Org. Chem.,* 40, 127 (1975) to give 3-(6-bicyclo[3.2.1]octanyl)-propionitrile. Following Examples 2-8, the propionitrile is converted to the 6-bicyclo[3.2.1]octanyl derivative related to the compound (IL).

EXAMPLE 75

Using the procedure of Example 1, 3-(1-bicyclo[3.3.1]nonanyl)propionitrile and 3-(3-bicyclo-[3.3.1]nonanyl)-propionitrile are respectively made from 1-bromo-bicyclo[3.3.1]nonane and 3-bromobicyclo[3.3.1]nonane. Following Examples 2-8, the propionitriles is converted to the compound (IM) and the related 3-bicyclo[3.3.1]nonanyl derivative.

EXAMPLE 76

Following the procedure of Example 74, bicyclo[3.3.1]-nonane-9-one is reacted to form the corresponding aldehyde, from which is made the corresponding 3-substituted propionitrile, which is then converted into the 9-bicyclo[3.3.1]nonanyl derivative related to the compound (IM).

EXAMPLE 77

Following the procedure of Example 74, 2-bicyclo[3.3.1]nonanecarboxaldehyde is reacted to form the corresponding 3-substituted propionitrile, which is then converted into the 2-bicyclo[3.3.1]nonanyl derivative related to the compound (IM).

EXAMPLE 78

Using the procedure of Example 1, 3-(1-noradamantyl)propionitrile is made from 1-bromonoradamantane, and 3-(2-noradamantyl)-propionitrile is made from 2-bromonoradamantane. Following Examples 2-8, the propionitrile is converted to the final compound (IN).

EXAMPLE 79

Following the procedure of Example 74, 3-noradamantanecarboxaldehyde is reacted to form the corresponding 3-substituted propionitrile, which is then converted into the 3-noradamantyl derivative related to the compound (IN).

EXAMPLE 80

Following the procedure of Example 74, noradamantane-7-one is reacted to form the corresponding aldehyde, from which is made the corresponding 3-substituted propionitrile, which is then converted into the 7-noradamantyl derivative related to the compound (IN).

EXAMPLE 81

Using the procedure of Example 1, 3-(1-bicyclo[2.2.2]octanyl)propionitrile is made from 1-bromobicyclo[2.2.2]octane and 3-(2-bicyclo[2.2.2]octanyl)propionitrile is made from 2-bromobicyclo[2.2.2]octane. Following Examples 2-8, the propionitriles are converted to the compound (IK) and the realted 2-bicyclo[2.2.2]octanyl derivative.

EXAMPLE 82

Using the procedure of Example 1, 3-(1-norbornenyl)propionitrile is made from 1-bromonorbornene. Following Examples 2-8, the propionitrile is converted to the compound (II).

EXAMPLE 83

Following the procedure of Example 74, 5-norborene-2-carboxaldehyde (a mixture of 2-endo and 2-exo) is reacted to form the corresponding 3-substituted propionitrile, which is then converted into the compound (IJ).

What is claimed is:

1. A compound of the formula 2-amino-7-(substituted methyl)-3H,5H-pyrrolo[3,2-d]pyrimidin-4-one wherein substituted methyl is —$CH_2$—R wherein R is a cycloolefin or cycloparafin having up to nine carbon atoms in the ring structure which can be optionally substituted with at least one of halogen, hydroxy, alkoxy, alkyl, or trifluoromethyl.

2. The compound of claim 1 wherein R is cyclopentyl, cyclohexyl, or cycloheptyl.

3. The compound of claim 1 wherein R is 1- or 2-adamantyl, 1- or 2-noradamantyl, 1-norbornanyl, 2-exonorbornanyl, 2-endonorbornanyl, 1- or 2-bicyclo[2.2.2]octanyl, 1-, 2-, 3-, 6-, or 8-bicyclo[3.2.1]octanyl, or 1-, 2-, 3-, or 9-bicyclo[3.3.1]nonanyl.

4. The compound of claim 1 wherein R is 1- or 2-norbornenyl.

5. The compound of claim 2 wherein R is substituted with at least one of chloro, fluoro, methoxy, ethoxy, propoxy, butoxy, methyl, ethyl, propyl, or butyl.

6. A method for the selective suppression of mammalian T-cell function without diminished effect on humoral immunity which comprises administering to a mammal the compound of claim 1, whereby said compound inhibits purine nucleoside phosphorylase and thereby T-cell formation.

7. A method for the selective suppression of mammalian T-cell function without diminished effect on humoral immunity which comprises administering to a mammal the compound of claim 2, whereby said compound inhibits purine nucleoside phosphorylase and thereby T-cell formation.

8. A method for the selective suppression of mammalian T-cell function without diminished effect on humoral immunity which comprises administering to a mammal the compound of claim 3, whereby said compound inhibits purine nucleoside phosphorylase and thereby T-cell formation.

9. A method for the selective suppression of mammalian T-cell function without diminished effect on humoral immunity which comprises administering to a mammal the compound of claim 4, whereby said compound inhibits purine nucleoside phosphorylase and thereby T-cell formation.

10. A pharmaceutical composition for the selective suppression of mammalian T-cell function without diminished effect on humoral immunity which comprises an effective amount of the compound of claim 1 capable of said selective suppression and a pharmaceutically acceptable carrier or diluent therefor.

11. A pharmaceutical composition for the selective suppression of mammalian T-cell function without diminished effect on humoral immunity which comprises an effective amount of the compound of claim 2 capable of said selective suppression and a pharmaceutically acceptable carrier or diluent therefor.

12. A pharmaceutical composition for the selective suppression of mammalian T-cell function without diminished effect on humoral immunity which comprises an effective amount of the compound of claim 3 capable of said selective suppression and a pharmaceutically acceptable carrier or diluent therefor.

13. A pharmaceutical composition for the selective suppression of mammalian T-cell function without diminished effect on humoral immunity which comprises an effective amount of the compound of claim 4 capable of said selective suppression and a pharmaceutically acceptable carrier or diluent therefor.

* * * * *